United States Patent
Maisenholder et al.

(10) Patent No.: US 6,873,764 B2
(45) Date of Patent: Mar. 29, 2005

(54) METHOD FOR PRODUCING A GRID STRUCTURE, AN OPTICAL ELEMENT, AN EVANESCENCE FIELD SENSOR PLATE, MICROTITRE PLATE AND AN OPTICAL COMMUNICATION ENGINEERING COUPLER AS WELL AS A DEVICE FOR MONITORING A WAVELENGTH

(75) Inventors: Bernd Maisenholder, Zürich (CH); Johannes Edlinger, Frastanz (AT); Claus Heine, Chur (CH); Michael Pawlak, Laufenburg (DE); Gert Duveneck, Bad Krozingen (DE)

(73) Assignee: Unaxis Balzers Aktiengesellschaft, Balzers (LI)

( * ) Notice: Subject to any disclaimer, the term of this patent is extended or adjusted under 35 U.S.C. 154(b) by 0 days.

(21) Appl. No.: 10/182,247

(22) PCT Filed: Jan. 26, 2001

(86) PCT No.: PCT/CH01/00060

§ 371 (c)(1),
(2), (4) Date: Nov. 18, 2002

(87) PCT Pub. No.: WO01/55760

PCT Pub. Date: Aug. 2, 2001

(65) Prior Publication Data

US 2003/0091284 A1 May 15, 2003

(30) Foreign Application Priority Data

Jan. 27, 2000 (CH) .............................................. 0160/00

(51) Int. Cl.[7] .............................................. G02B 6/34
(52) U.S. Cl. ................................................................ 385/37
(58) Field of Search ........................... 385/4, 8, 14, 12, 385/31, 129–132, 37; 422/82.11; 250/227.11, 237 G, 458.1, 459.1; 356/135–137, 128

(56) References Cited

U.S. PATENT DOCUMENTS

| | | |
|---|---|---|
| 5,675,691 A | 10/1997 | Edlinger et al. |
| 5,738,825 A | 4/1998 | Rudigier et al. |
| 5,822,472 A | 10/1998 | Danielzik et al. |

FOREIGN PATENT DOCUMENTS

| | | |
|---|---|---|
| CH | 688 165 | 5/1997 |
| EP | 0 508 359 | 3/1994 |
| EP | 0 602 829 | 6/1994 |

OTHER PUBLICATIONS

Day et al., "Filter–Response Line Shapes of Resonant Waveguide Gratings," Journal of Lightwave Technology, US, IEEE, NY, Aug. 1, 1996, pp. 1815–1824.

Dubendorger et al, "Compact Integrated Optical Immunosensor using Replicated Chirped Coupling Grating Sensor Chips," Applied Optics, 37/10, Apr. 1, 1998.

Primary Examiner—Tu T. Nguyen
(74) Attorney, Agent, or Firm—Crowell & Moring LLP (57) ABSTRACT

A coupling grating formed as a line grating with a grating period between 100 nm and 2500 nm, a substrate (1) is covered with a photoresist layer (10) and exposed for instance at the Lithrow angle ($\Theta_L$) or at 0° to a mercury-vapour lamp (11) via a folding mirror (13, 13') through a phase mask (14) in the near field of which the photoresist layer is arranged, then structured by reactive ion etching and provided with a transparent layer by reactive DC magnetron sputtering, particularly pulsed DC sputtering or AC-superimposed DC sputtering. The phase mask (14) is structured in advance with the laser two-beam interference method. The process is particularly suited for the production of optical elements, particularly evane-scent field sensor plates and optical couplers for communications technology which can be employed in particular as filters for wavelength multiplexing in fibre-optic networks.

30 Claims, 9 Drawing Sheets

METHOD FOR PRODUCING A GRID STRUCTURE, AN OPTICAL ELEMENT, AN EVANESCENCE FIELD SENSOR PLATE, MICROTITRE PLATE AND AN OPTICAL COMMUNICATION ENGINEERING COUPLER AS WELL AS A DEVICE FOR MONITORING A WAVELENGTH

FIELD OF THE INVENTION

The invention relates to a process for producing at least one continuous grating structure an optical element produced with the aid of the process according to the invention, as well as an evanescent field sensor plate and a microtitre plate and an optical coupler for communications technology, furthermore a device for monitoring a wavelength containing such a coupler.

The process according to the invention is suitable for producing optical elements with grating structures. Evanescent field sensor plates and microtitre plates produced according to the process can be used in chemical and biomolecular analyses. The applications of optical couplers are in communications technology, and more particularly in data transmission via fibre networks. A potential application of a particular coupler according to the invention is in a device for monitoring the wavelength of laser light in a fibre network.

PRIOR ART

From EP-A-0 602 829 a process for producing a grating structure on a substrate, for example for a DBR semiconductor laser, is known in which first a phase mask is produced and then the substrate, e.g. InP, is exposed at the Lithrow angle through the phase mask. The exposure can be to a Hg—Xe arc lamp having a light source diameter of 0.25 mm, three lines around 365 nm wavelength being filtered out. The substrate is located in the near field of the phase mask, i.e. at a distance of at most 10 μm.

To produce the phase mask, a quartz substrate is covered with three layers, a photoresist layer, a thin germanium layer and finally a layer of a resist sensitive to electron beams. The uppermost layer is then structured by electron beam writing, developing the uppermost layer and removing the unexposed parts. The structure is transferred to the layers underneath by reactive ion etching, initially with $CF_3Br$ and then with $O_2$, and finally to the quartz substrate itself by a further step of reactive ion etching, whereupon the residues of the layers are removed. The grating period may be, for example, between 190 nm and 250 nm. The phase mask may be several centimetres long and the grating may extend over its entire length. However, as a rule, the length of the lines is only 5–20 μm. Greater lengths are possible but require very long processing times. In practice, gratings of more than 1 $mm^2$ can scarcely be produced with reasonable effort and good accuracy. In particular, stitching errors can hardly be avoided during electron beam writing.

From U.S. Pat. No. 5,675,691 a plate is known on which coupling gratings are produced by applying a layer of $TiO_2$, $Ta_2O_5$, $HfO_2$, $Y_2O_3$, $Al_2O_3$, $Nb_2O_5$, nitride or oxynitride of Al, Si or Hf to a substrate of glass, in particular quartz glass, ceramic, or predominantly organic material, it being possible to provide a 20 nm thick intermediate layer, e.g. of $SiO_2$, and to structure it by ablation or modification of the refractive index by means of exposure to two superimposed beams of an excimer laser or to a beam modified by a mask. Instead, it is also possible to structure an intermediate layer, e.g. of $TiO_2$, in which the ablation barrier is lower and which is applied either to the layer or directly to the substrate and, in the latter case, is superimposed by the layer after structuring. The grating periods are, for example, 375 nm or 440 nm. The grating surface area is freely selectable and may be, for example, 1 mm×1 mm or 8 mm×8 mm.

From U.S. Pat. No. 5,822,472 an evanescent field sensor plate for chemical analyses is known which bears a 40 nm to 160 nm thick layer of $TiO_2$, ZnO, $Nb_2O_5$, $Ta_2O_5$, $HfO_2$ or $ZrO_2$ on a support of plastic, glass, or quartz. An intermediate layer of nonluminescent material with a low refractive index, e.g., quartz having a thickness of 100 nm, for example, which at the same time serves as an adhesion promoter, may be arranged in between. An input coupling grating and an output coupling grating are provided which are created by known photolithographic or holographic and etching methods, either in the support or in the layer, and have a grating period of between 200 nm and 1000 nm. The gratings may have dimensions of 2 mm (parallel to the lines)×4 mm, with a total surface area of the wave-guide plate of 12 mm×20 mm.

From J. Dübendorfer and R. E. Kunz: "Compact integrated optical immunosensor using replicated chirped coupling grating sensor chips", Applied Optics, 37/10 (Apr. 1, 1998), a further evanescent field sensor plate comprising a polycarbonate support plate is known into which a modulated input coupling grating having a grating period varying between 420 nm and 422.8 nm and an output coupling grating having a grating period varying between 595.1 nm and 600.8 nm were embossed. Thereafter, a $TiO_2$ layer having a thickness of 137 nm and a refractive index of 2.346 was applied by means of low-temperature DC magnetron sputtering, and finally the evanescent field sensor plate was silanised. The input coupling angle is about −9.5° and the output coupling angle is about 22.5°.

From U.S. Pat. No. 5,738,825 a microtitre plate can be gathered which has a 20 nm to 1000 nm, preferably 30 nm to 500 nm thick layer of $TiO_2$, $Ta_2O_5$, $HfO_2$, $ZrO_2$, $SiO_2$, $Si_3N_4$, $Al_2O_3$, $Nb_2O_5$ nitride or oxynitride of Al, Si or Hf applied to its bottom surface, this layer being covered by a plastic layer. Input and output coupling gratings are mounted underneath each cavity. The gratings have a grating period between 330 nm and 1000 nm, in particular about 400 nm to 800 nm, and are produced by lithographic or mechanical methods.

From CH-A-688 165 a wave-guide plate comprising a substrate of plastic, e.g. polycarbonate, is known whose surface was structured mechanically—by deep drawing, embossing or during its injection moulding—and in particular provided with a coupling grating, and bears a layer of $TiO_2$, $Ta_2O_5$, $ZrO_2$, $Al_2O_3$, $SiO_2$—$TiO_2$, $HfO_2$, $Y_2O_3$, $Nb_2O_5$, silicon nitride, oxynitride, $SiO_xN_y$, $HfO_xN_y$, $AlO_xN_y$, $TiO_xN_y$, $MgF_2$ or $CaF_2$ applied by a PVD method. To reduce the attenuation losses, an approximately 20 nm thick intermediate layer applied to the substrate prior to the layer and comprising an inorganic dielectric material such as $SiO_2$ is provided which at the same time serves as an adhesion promoter.

All plates described above are produced by processes with which no satisfactory uniformity of the coupling grating can be achieved, so that the coupling angle varies relatively widely. Consequently, the relative angular position of the exposure unit and plate must be optimised laboriously in each step when the plate is to be used as an evanescent field sensor plate. The filter characteristics are unsatisfactory and not sufficient, for instance, for selectively filtering a particular wavelength from a group of very closely spaced wavelengths, when the plate is used as an optical coupler in communications technology. Some of the processes described are also very laborious or do not allow very large numbers of pieces of constant quality to be made.

SUMMARY OF THE INVENTION

It is the object of the invention to provide a process which permits the production, particularly the volume production, of lattice structures with high precision and relatively low effort.

Using the process according to the invention it is also possible to produce large-area lattice structures, particularly continuous grating structures which are long in a direction parallel to the lines, with high precision throughout, and in a simple and economical way. Moreover, a large freedom of design is secured with respect to the arrangement and shape of the grating structures. Hence the production of highly different optical elements for diverse applications is feasible with one and the same installations. The process according to the invention furthermore permits the production of large series of optical elements of constant quality and with optical properties such as coupling efficiencies and, in particular, coupling angles which are constant within narrow limits.

Furthermore, a highly precise optical element is to be provided such as can be produced by the process according to the invention. In particular, the optical element can be formed as an evanescent field sensor plate or as a microtitre plate based on such a plate. In view of the narrow limits within which, even in long gratings, the coupling angle varies, it is possible to simultaneously illuminate and read out larger parts of the evanescent field sensor plate or microtitre plate. Successive exposure of different parts of the evanescent field sensor plate or microtitre plate is also simplified since reoptimisation of the relative angular position of this plate and the exposing unit is not required or in any case greatly simplified.

The optical element can also be formed as an optical coupler for communications technology. In this case, the high precision present even in large grating structures guarantees excellent filter characteristics, and particularly a very-narrow-band selection of individual wavelengths, so that for instance a wavelength multiplexing involving very closely spaced wavelengths is possible, which raises the transmission capacity.

BRIEF DESCRIPTION OF THE DRAWINGS

The invention is explained in more detail below with reference to figures merely representing an embodiment.

FIG. 2 shows a section along II—II in FIG. 1, FIG. 3 schematically shows the use of a microtitre plate comprising an evanescent field sensor plate according to the invention.

DESCRIPTION OF EMBODIMENTS

The process according to the invention will in the following be explained in more detail in connection with an evanescent field sensor plate and its production. Here, an evanescent field sensor plate is understood as a plate making it possible by illumination of one part of the surface to create an evanescent field in the reach of which a sample to be analysed may be arranged. Therefore, evanescent field sensor plates serve the purposes of chemical analysis. Evanescent fields are nonradiating electromagnetic fields which fall off and vanish with increasing distance from the scattering surface at which they are generated. Such fields can arise in connection with spatial modulations of the electric field in the plane having periodicities smaller than one wavelength. The best-known example of such a modulation occurs at an interface between a dielectric and air when a light beam coming from the side of the dielectric has an angle of incidence larger than the critical angle.

Evanescent field sensor plates have a transparent light-directing layer from which the evanescent light leaves their surface, and interacts with bound molecules present there, for instance exciting their luminescence. The evanescent field sensor plate consists (FIGS. 1, 2, the diagrams are schematic and not to scale) of a glass substrate 1, for example AF 45 of Schott DESAG measuring 102 mm×72 mm and having a thickness of 0.7 mm, which on one side bears a transparent layer 2 of $Ta_2O_5$ having a thickness of 150 nm. Its refractive index is 2.11 at a wavelength of 633 nm.

Figure 1:
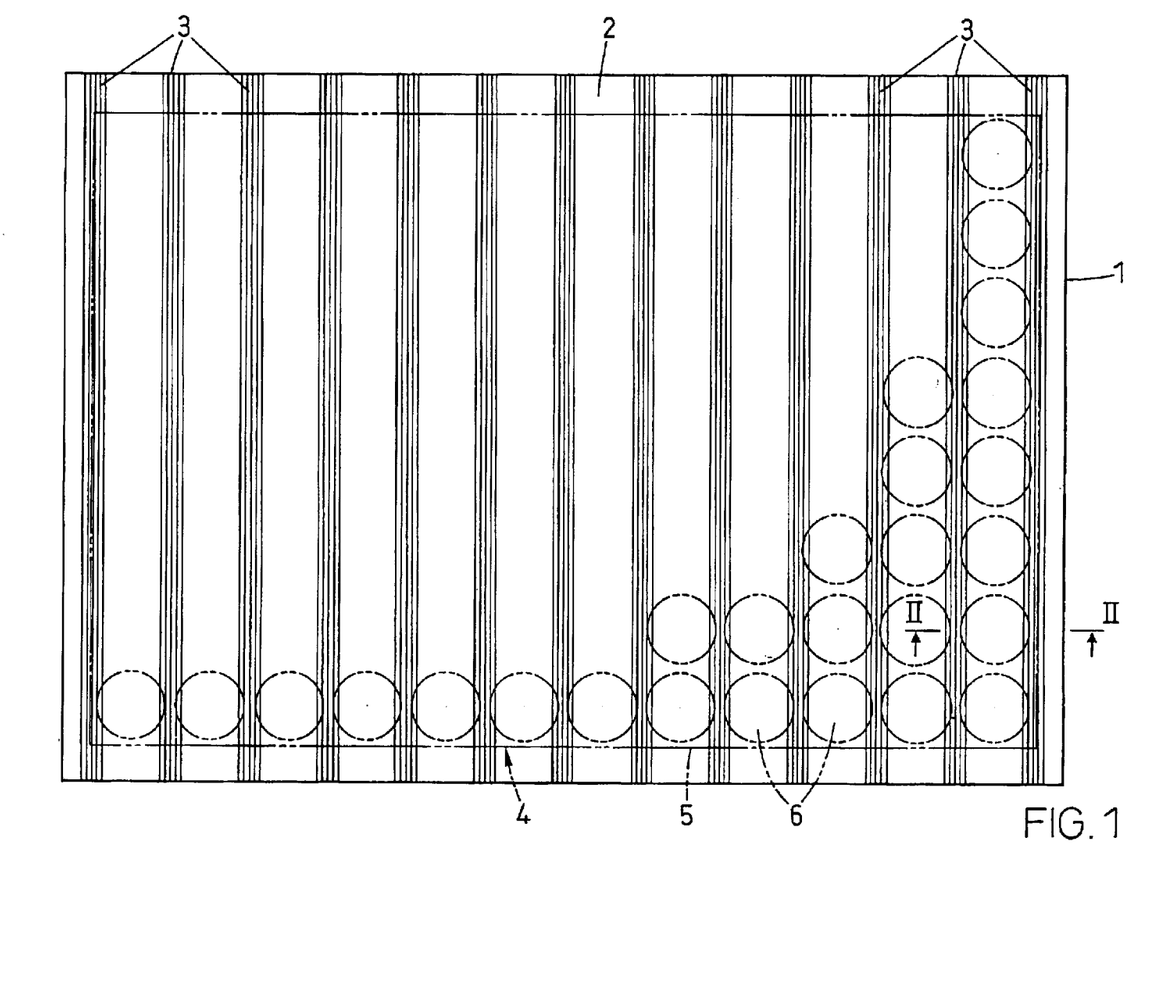
FIG. 1 shows a plan view of an evanescent field sensor plate according to the invention, having an added top piece indicated by dashed lines so that it becomes a complete microtitre plate.
Figure 2:
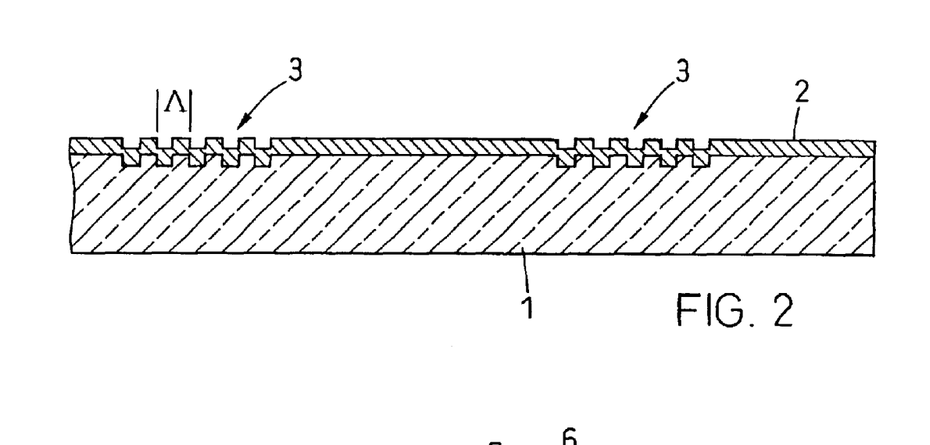

A plurality of coupling gratings 3 in the form of parallel, spaced apart strips which extend parallel to the lines over the entire width of the evanescent field sensor plate are arranged on the surface bearing the layer 2. The width of each of the strips is 0.5 mm. The grating period Λ=360 nm, the groove-to-land ratio is about 1:1, and the grating depth is about 20 nm. The parameters defining the grating are very precisely preserved over the full length of all strips. Consequently, changes in the coupling angle Θ at which a light beam directed from below through the substrate 1 to the coupling grating 3, in particular a light beam having a wavelength of about 633 nm, is coupled into the layer 2 with maximum coupling efficiency remain within very narrow limits. Along the lines of a coupling grating 3, it changes by at most 0.05°/cm. Over the entire evanescent field sensor plate, the deviation of the coupling angle Θ from a mean value which, in the case described, corresponds to 2.31° remains below 0.15°.

The surface of layer 2 is provided with a coating consisting of an adhesion promoter layer, preferably of at least one chemical compound selected from the group of silanes, epoxides, and self-organising functionalised monolayers, and on top of it a layer of molecular recognition elements such as nucleic acids, antibodies, antigens, membrane receptors, and their ligands.

Figure 3:
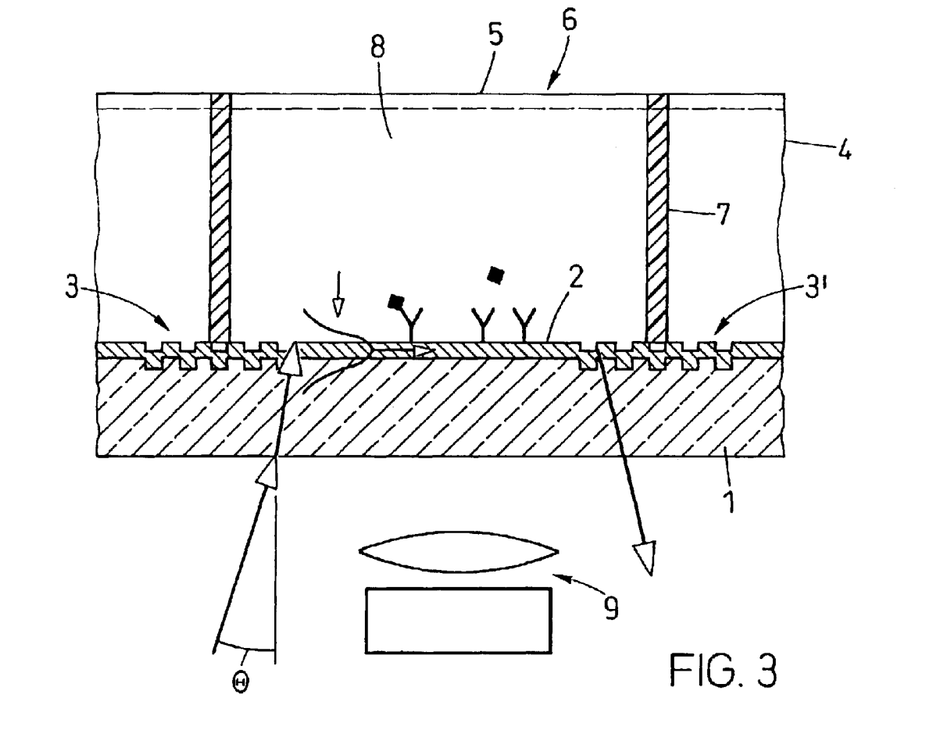

As shown in FIG. 3 and indicated in FIG. 1, the evanescent field sensor plate is extended by an added honeycomb-like top piece 4 of plastic to form a microtitre plate to be employed for chemical analysis, in particular of biological substances. The top piece has a cover plate 5 which is perforated by round openings 6 having a diameter of, for example, about 8 mm which are arranged as a regular array. At the bottom side of cover plate 5, a tube section 7 is attached to each of the openings which is open at the bottom, laterally delimits a cavity 8, and is tightly bonded, for example glued, at its lower end to the evanescent field sensor plate 2.

If it is intended to investigate the contents of a cavity 8, for instance an analyte such as blood, serum, urine, saliva, or a solution containing a drug candidate, with respect to the concentration of specific molecules, an adjacent coupling grating 3 of the evanescent field sensor plate 2 is exposed in a manner known per se to a suitable light source at the coupling angle Θ, the light having a specific wavelength, in the example to light with a wavelength of 633 nm, by means of a He—Ne laser. The light is conducted through the layer 2 forming the bottom of the cavity 8 to the adjacent coupling grating 3', and there coupled back out. The evanescent light stimulates fluorescence in molecules in the cavity 8 which are bound to recognition elements, which fluorescence is recorded by an optical system 9 and then analysed. The high precision with which the coupling angle Θ is preserved over the length of the coupling grating 3 permits a simultaneous and highly efficient examination of the cavities arranged along the same. Since over the entire evanescent field sensor plate 2, the coupling angle Θ departs but slightly from the mean value, no laborious optimisation of this angle is required even when examining the next row of cavities 8. As an alternative or in addition to evaluating the fluorescence, one can also record changes in the refractive index produced at the bottom of cavity 8 by the binding of molecules to the recognition elements.

Figure 4A:
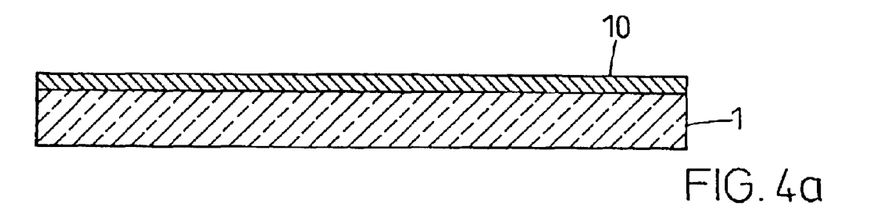
FIGS. 4a–e show different steps in the production of an evanescent field sensor plate according to the invention, FIG. 5 schematically shows the setup used for exposing the photoresist layer during production of the evanescent field sensor plate according to the invention.

As shown schematically in FIGS. 4a–e, to produce the transparent layer 2, one first applies a photoresist, e.g. AZ1518, diluted 1:4 with AZ1500, both of Clariant, at 1300 rpm to the substrate 1 and then bakes for 30 min at 90° C. in an oven, whereupon Aquatar of the same manufacturer is applied at 1400 rpm and once again baked for 15 min at 90° C. in the oven. The photoresist layer 10 thus produced has a thickness of less than 200 nm, as a rule of about 150 nm, so that interfering standing waves will not develop in it. The reflectivity is below 1%, so that interfering reflections which could lead to the development of Newton's rings are also practically excluded (FIG. 4a).

Figure 5:
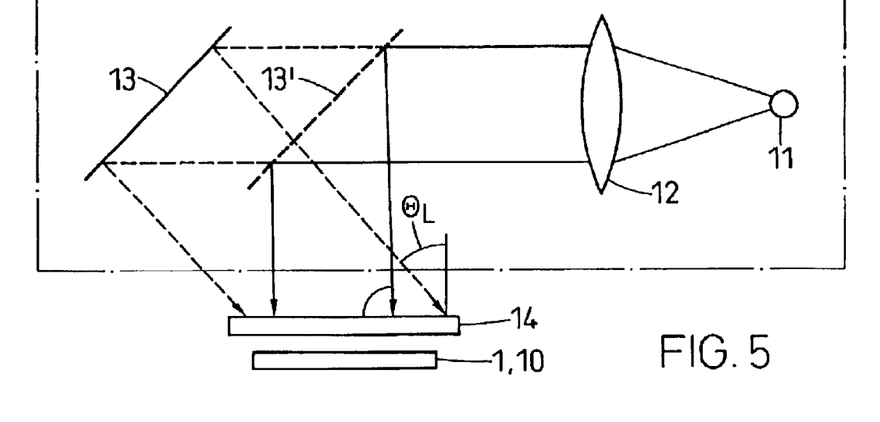

In a subsequent step, the photoresist layer 10 is exposed for 70 s. For this purpose, the substrate 1 is introduced into the setup according to FIG. 5, which is a mask aligner MA4 of Süss, Munich, comprising a modified mercury-vapour lamp 11 having a modified end-stage optical system 12 and folding mirror 13. The optical system 12 comprises a bandpass filter which, for example, filters out the I-line at a wavelength of 365 nm, and a polarizer, which preferably produces s-polarised light. To improve the parallelism of the beams, the fly's eye is removed from the beam path, a lamp with as small an arc as possible is used and is positioned as far away from the substrate as possible.

Figure 7A:
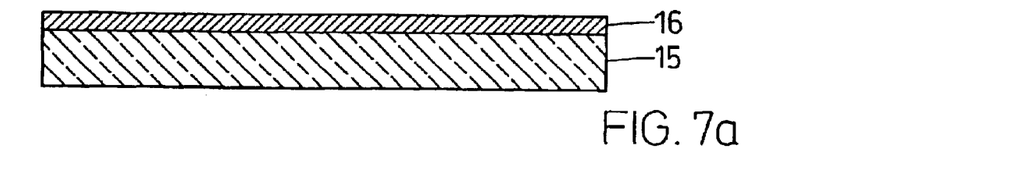
FIGS. 7a–g show different steps in the production of a phase mask for the production of an evanescent field sensor plate according to the invention.
Figure 7B:
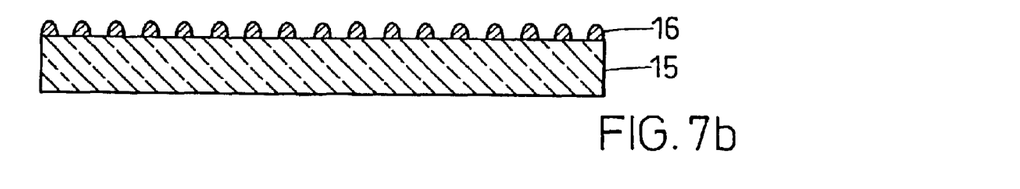
Figure 7C:
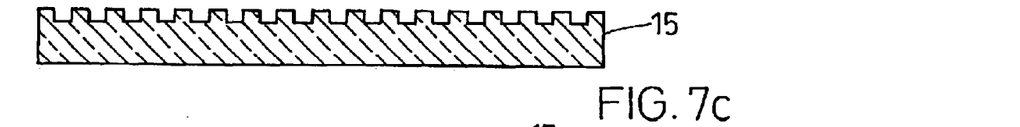
Figures 7D, 7E, 7F:
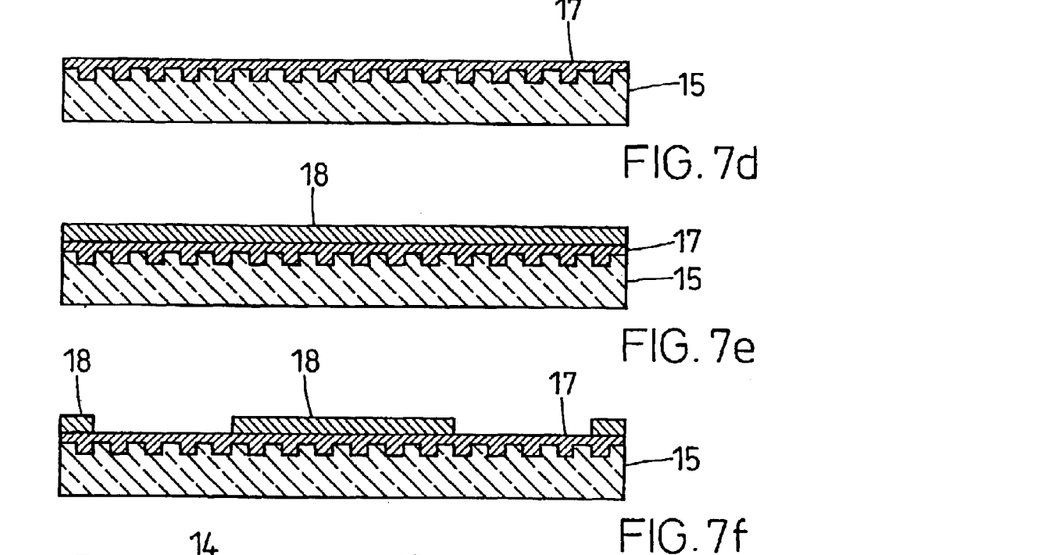
Figure 7G:
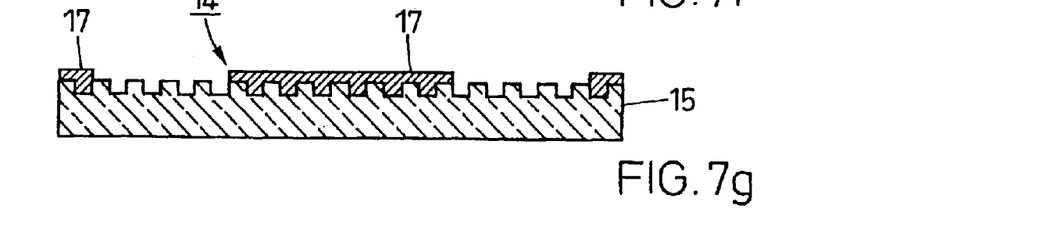

The exposure occurs through a phase mask 14. It comprises a substrate of transparent material, in the example quartz, with a large-area grating structure, a diffraction grating bearing a layer of nontransparent material, in the example chromium, which is interrupted—in the example, by regularly spaced, consecutive strips. Phase masks of this type are supplied by Ibsen in Farum (Denmark), and are manufactured approximately as follows:

A quartz substrate 15 is covered with a photoresist layer 16 (FIG. 7a) and the latter is exposed to light using the laser two-beam interference method, and developed (FIG. 7b). Then a full-area diffraction grating is produced on the surface of the quartz substrate 15 by etching and subsequent removal of the photoresist (FIG. 7c). Said surface is then completely covered with a chromium layer 17 (FIG. 7d). A continuous photoresist layer 18 is then applied to the chromium layer 17 (FIG. 7e) and exposed through a mask structured by electron beam or laser writing. The photoresist is then developed (FIG. 7f) and the chromium layer 17 is removed by etching from the parts not covered by photoresist. Finally, the residues of the photoresist layer 18 are removed to finish the phase mask 14 (FIG. 7g). The structure of the mask thus determines which parts of the phase mask are transparent.

Figure 6:
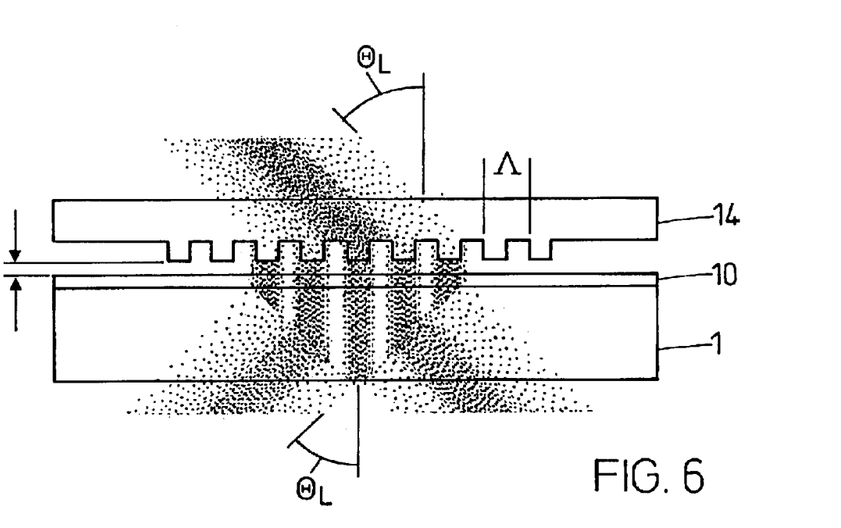
FIG. 6 shows the photo mask and substrate with the photoresist layer under exposure.

The substrate 1 is arranged underneath the phase mask 14 in such a way that the photoresist layer 10 is in vacuum contact with said phase mask. The upper side of the phase mask 14 is exposed at an angle which approximately corresponds to the Lithrow angle $\Theta_L$, which is the angle at which the angle of incidence is equal to the angle of first-order diffraction, and in particular deviates by no more than 10°, preferably by no more than 5°, from said angle. Under these conditions, a pronounced diffraction pattern whose structure corresponds to that of the grating of the phase mask 14 forms in the near field below the transparent regions of the phase mask 14 (FIG. 6). Alternatively, the phase mask 14 can also be exposed at an angle which approximately corresponds to 0°, i.e., vertical incidence, or at an angle that does not deviate from it by more than 10°, preferably not by more than 5° (folding mirror 13' shown in dashed lines). In this case, the diffraction pattern in the near field of the phase mask 14 has half the grating period of that mask.

Figure 4B:
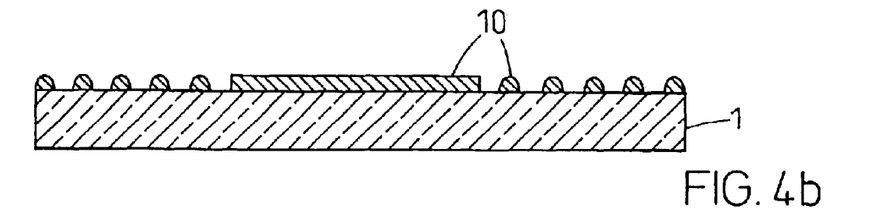
Figure 4C:
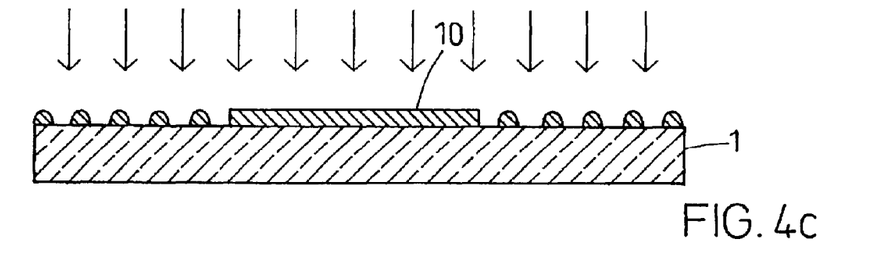
Figure 4D:
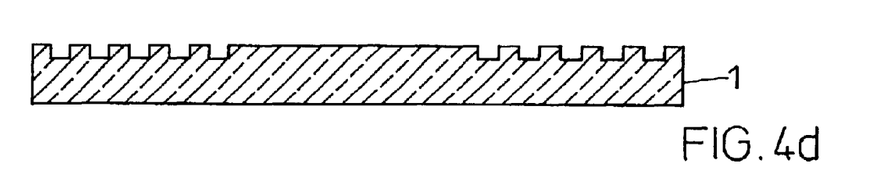

After exposure the Aquatar layer is removed by washing with deionized water, and the photoresist is then developed (FIG. 4b). Those parts of the surface of substrate 1 which are not covered with photoresist are then etched with Ar and $CHClF_2$ at a pressure of 0.02 mbar in a parallel-plate reactor with capacitive excitation of the plasma at 13.6 MHz and an RF power of 50 W. The etch depth is 20 nm. The photoresist is then removed. For this purpose, it is first subjected to reactive ion etching for 60 s in an oxygen plasma at a pressure of 0.2 mbar and an RF power of 50 W, then detached with Remover AZ100, Deconex, and deionized water (FIG. 4d).

Figure 4E:
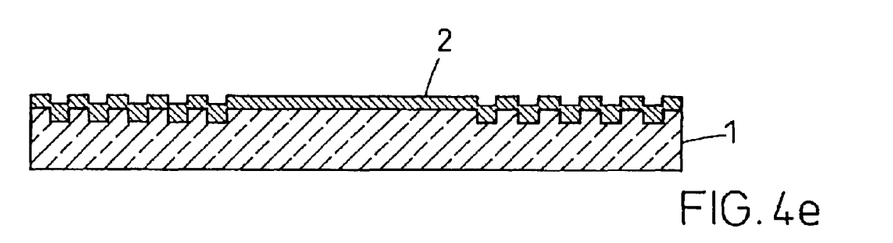

Finally the layer 2 is applied by reactive pulsed DC magnetron sputtering or by DC magnetron sputtering superimposed with an AC frequency between 1 kHz and 1 MHz, in a Balzers MSP1000 unit, similarly as described in EP-A-0 508 359 (FIG. 4e). This step is carried out in an Ar—$O_2$ atmosphere at a pressure of 3.7 μbar. The target material is tantalum. Finally, the evanescent field sensor plate is cut to its final size by wafer sawing.

Particularly on account of exposure through a phase mask that can be reused practically as often as desired, the process described permits the production of elements with grating structures, particularly diffractive coupling gratings, in large numbers and in a simple manner. The fact that the phase mask is structured by the two-beam interference method also implies that large defect-free grating structures having surface areas of 10 $cm^2$ and more can be produced on it with high precision, whereas other structuring methods such as electron beam writing are not suitable for this purpose owing to their virtually unavoidable stitching errors. Therefore, large optical elements with large-area gratings of high quality and uniformity can be produced, not only as final products but also as semi-finished plates which by wafer sawing, scribing and breaking or laser cutting can then be separated into smaller final products which thus can be produced very economically and in high quality.

Evanescent field sensor plates can of course also be produced in geometries and optical properties corresponding to other standards or requirements. Thus, another evanescent field sensor plate can have dimensions of 57 mm×14 mm×0.7 mm and be provided with two strip-shaped coupling gratings having a width of 0.5 mm each which are symmetrically arranged in parallel with the long sides, and have a mutual distance of 9 mm. The grating period Λ=318 nm, the grating depth 12 nm, while otherwise the properties of the layer and coupling gratings are the same as in the first example. In this case the coupling angle Θ=−12.14° at a wavelength of 633 nm, varying parallel to the lines by at most 0.15°/cm. The deviation from a mean value remains below 0.5° everywhere on the evanescent field sensor plate. For the production of a semifinished plate from which the individual evanescent field sensor plates are then obtained by wafer sawing, a phase mask is employed which measures 150 mm×150 mm and has a region with a grating of grating period 318 nm measuring 115 mm×115 mm. The regions corresponding to the coupling gratings are bare while the remaining portion of the grating is again masked by a nontransparent layer, particularly a chromium layer. Otherwise the production proceeds as described above.

A further example is an evanescent field sensor plate measuring 75 mm×113.5 mm×0.7 mm which as to its basic features essentially corresponds to FIG. 1, and which bears 13 strip-shaped coupling gratings each 0.5 mm wide which are parallel to the broadside and have distances between neighboring strips of 8.5 mm each. Layer and grating properties correspond to those of the second example. The coupling angle Θ=−11.48° at a wavelength of 633 nm, varying parallel to the lines by at most 0.05°/cm. Over the entire evanescent field sensor plate it departs from a mean value by at most 0.4°. The evanescent field sensor plate can be expanded to a microtitre plate with 8×12 cavities by adding a suitable top portion.

Apart from the embodiments of optical elements having grating structures produced by the process according to the invention and used in chemical analysis, as portrayed above, embodiments for applications in communications technology are particularly pertinent. Such elements are suited above all as highly efficient optical couplers such as those employed in fibre-optic networks.

Figure 8A:
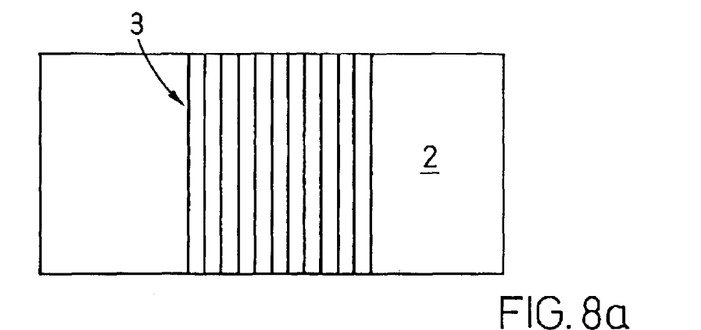
FIG. 8a schematically shows a plan view of a first embodiment of an optical coupler for communications technology according to the invention, FIG. 8b schematically shows a central section through the coupler according to FIG. 8a, FIG. 9a schematically shows the reflectivity of the coupler according to the first embodiment.
Figure 8B:
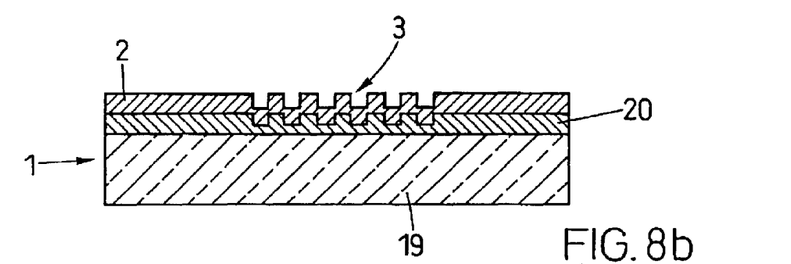
Figure 9A:
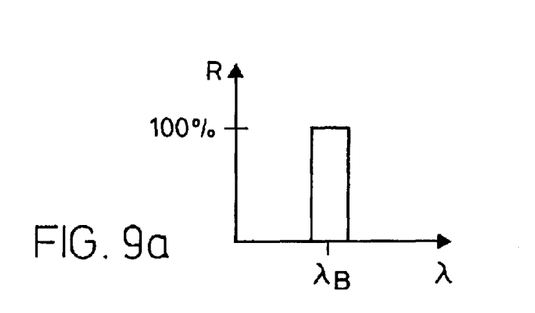
Figure 9B:
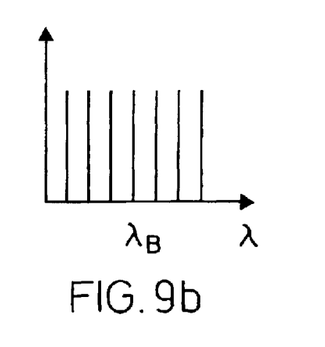
FIGS. 9b–d show diagrams showing the selection of a wave-length by the coupler according to the first embodiment.
Figures 9C, 9D:
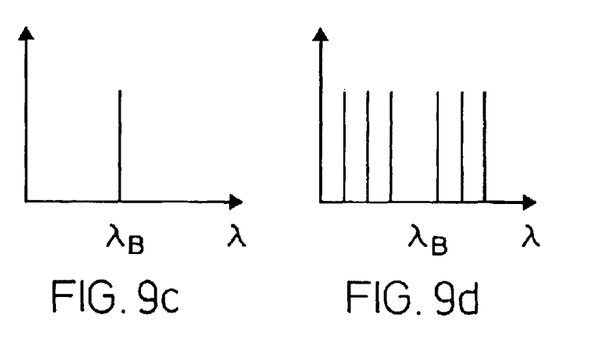

A first example of such a coupler is represented in FIGS. 8a and 8b. On a substrate 1 consisting of a glass plate 19 and a layer 20 of transparent material, a coupling grating 3 formed as a line grating of constant grating period is arranged. The layer 20 is covered by a transparent layer 2, consisting for instance of $Ta_2O_5$. Layer 2 acts as a waveguide. The coupling grating 3 reflects light of a particular wavelength $\lambda_B$ according to the wavelength-dependent reflectivity R schematically represented in FIG. 9a, while incident light of all other wavelengths is transmitted. This is shown in FIGS. 9b–d, where FIG. 9a shows the incident wavelengths, FIG. 9b the reflected wavelength $\lambda_B$, and FIG. 9c the transmitted wavelengths. Using the coupler it is thus possible to filter out a particular wavelength, for instance in a fibre-optic network using wavelength multiplexing. Thanks to the high grating quality, the full width at half maximum of the reflectivity R as a function of wavelength is very small. Hence even with wavelengths very closely spaced, it is possible to highly efficiently separate a wavelength.

Figure 10:
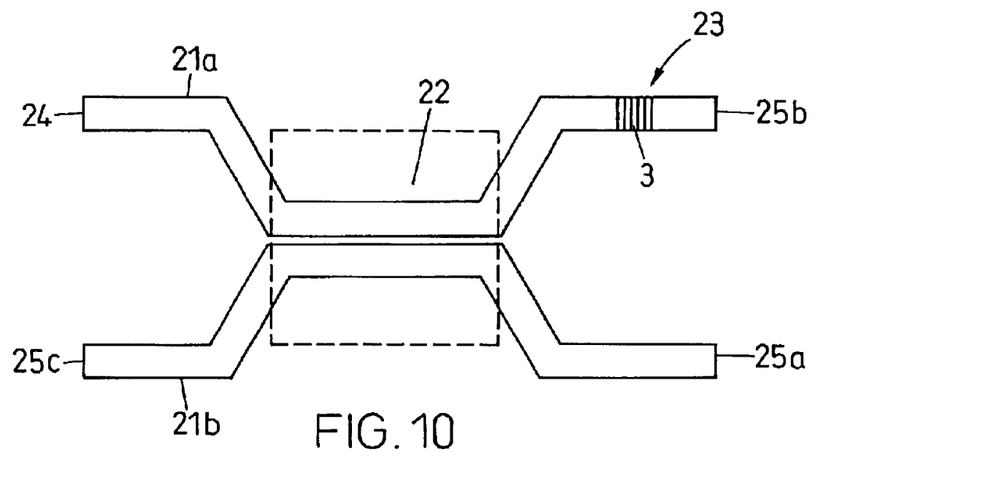
FIG. 10 shows an arrangement with a coupler according to the first embodiment, FIG. 11a schematically shows a plan view of a second embodiment of an optical coupler for communications technology according to the invention, FIG. 11b schematically shows a central section through the coupler according to FIG. 11a, FIG. 12 shows an arrangement with a coupler according to the second embodiment, FIG. 13a schematically shows a plan view of a third embodiment of an optical coupler for communications technology according to the invention, FIG. 13b schematically shows a central section through the coupler according to FIG. 13a, FIG. 14 shows a device for monitoring and stabilising the wavelength of a light beam emitted by a laser which comprises a coupler according to the third embodiment.

An example for the use of such a coupler is shown in FIG. 10. Two parallel stripe waveguides 21a, b of known structure are running parallel at a very small mutual distance in a coupling region 22, in such a way that 50% of the light conducted in the first stripe waveguide 21a is transferred to the second stripe waveguide 21b, and vice versa. In the final segment of the first stripe waveguide 21a, a coupler 23 with a coupling grating 3 according to FIGS. 8a and b is incorporated which selectively reflects light having a wavelength $\lambda_3$.

When signals having wavelengths $\lambda_1$, $\lambda_2$, $\lambda_3$, $\lambda_4$ etc. are fed into the first stripe waveguide 21a at an input 24, then on one hand 50% of all signals in the coupling region 22 are transferred to the second stripe waveguide 21b where they are conducted to a first output 25a, while the signals remaining in the first stripe waveguide 21a are conducted to a second output 25b, except for the signal of wavelength $\lambda_3$ corresponding to the $\lambda_B$ according to FIGS. 9a–d which is reflected at the coupler 23 so that in the coupling region 22, 50% of its intensity transfer into the second stripe waveguide 21b where the signal is conducted in a direction opposite to that of the signals transferred directly from the first stripe waveguide 21a, and reaches a third output 25c where finally it has been isolated and can be further processed. The signals of outputs 25a and b can be recombined to a signal differing from the original one only by a 50% attenuation of the signal with wavelength $\lambda_3$.

The coupler 23 can be completely integrated into the first stripe waveguide 21a, in such a way that this has the same structure as coupler 23 and this coupler forms a single part with the first stripe waveguide 21a. The only distinction of coupler 23 is then its bearing the coupling grating 3.

Figure 11A:
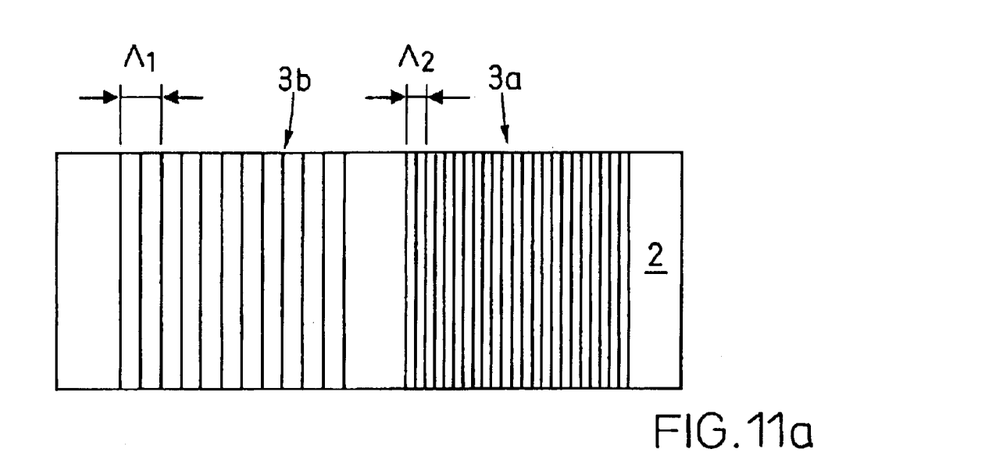
Figure 11B:
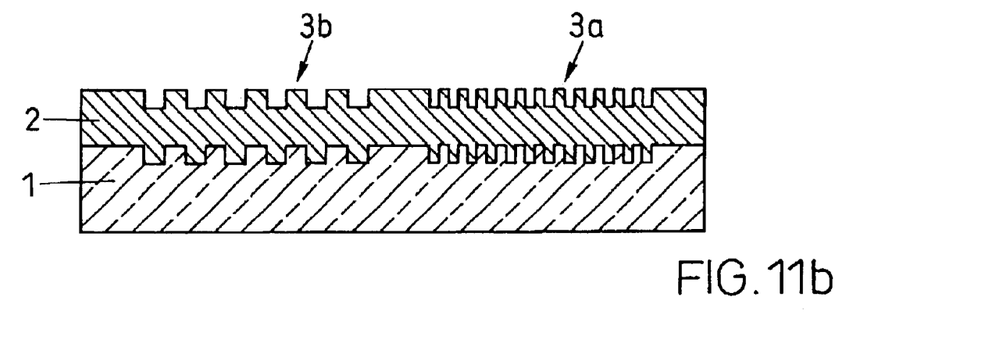

A second example of a coupler is represented in FIGS. 11a and b. In a longitudinal direction on top of a rectangular substrate 1 of glass, for instance Schott DESAG AF 45 with a refractive index of 1.52, two coupling gratings, an input coupling grating 3a and an output coupling grating 3b, are arranged consecutively at a mutual distance, each extending over the full width of the coupler. The input coupling grating 3a has a grating period of $\Lambda_1$=981 nm and a grating depth of 6 nm, the output coupling grating 3b has a grating period of $\Lambda_2$=1350 nm and a grating depth of 12 nm. The upper side of substrate 1 is covered by a continuous transparent layer 2 consisting of $Ta_2O_5$ and having a refractive index of 2.1. Its thickness is 400 nm.

Figure 12:
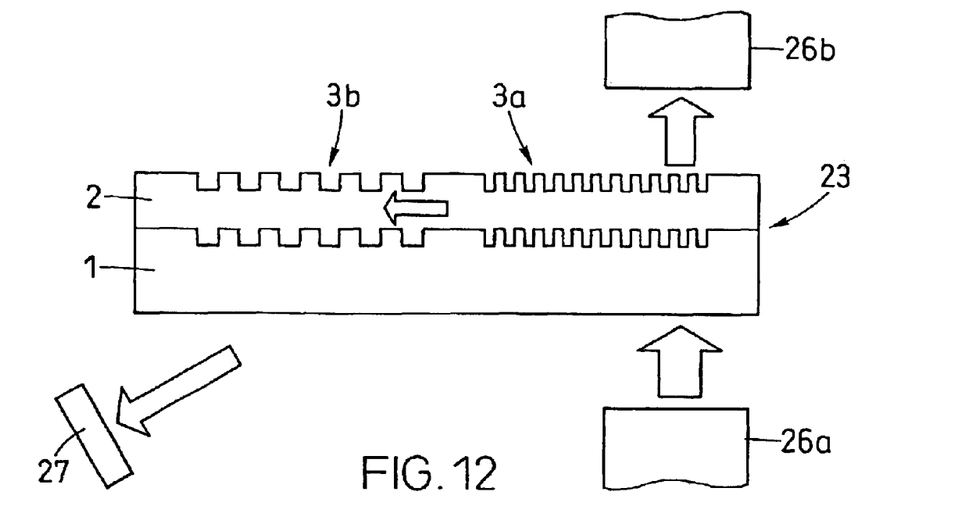

The coupler can be used as a drop filter monitoring and stabilising the intensity of a light beam, for instance a line of a multimode laser. To this end (FIG. 12), the coupler 23 described above is so arranged between the ends of a first optical fibre 26a and a second optical fibre 26b arranged in the continuation of the former that the input coupling grating 3a faces the end of the latter while the former faces the bottom side of coupler 23. The light supplied by the first optical fibre 26a passes through the part of the coupler 23 carrying the input coupling grating 3a while a fraction of the light of the 1550 nm line corresponding to less than 0.01% of its intensity is coupled into the layer 2 by said grating. At the output coupling grating 3b, light is coupled out at an angle of 30° and reaches an appropriately disposed photo-detector 27 the output signal of which is a measure of intensity of the monitored line. Owing to the high precision of the input coupling grating 3a, the input coupling is highly wavelength-sensitive, the full width at half maximum of the intensity distribution being a mere 0.01 nm, so that a specific monitoring of a single wavelength is possible even where the wavelengths are closely spaced, as desired in wavelength multiplexing in the interest of a high transmission capacity.

Figure 13A:
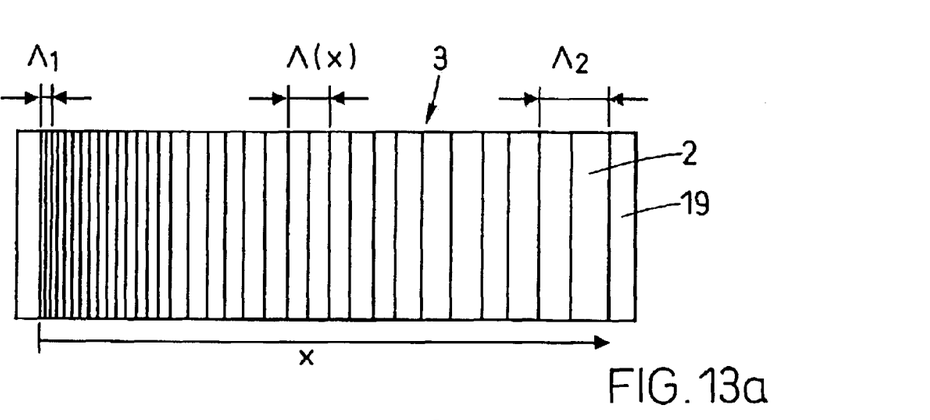
Figure 13B:
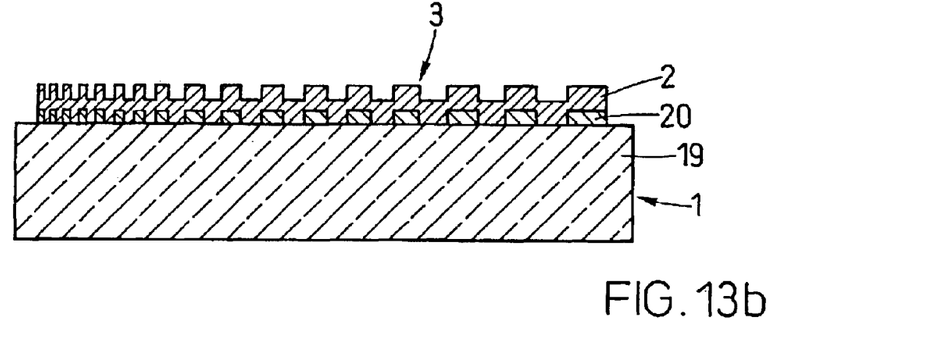

A third example of an optical coupler according to the invention is represented in FIGS. 13a and b. A rectangular substrate 1 consists of a glass plate 19 with a refractive index of 1.586 and a transparent layer 20 of $TiO_2$ with a refractive index of 2.4 covering the upper face of this glass plate in a thickness of 285 nm. The upper face bears a coupling grating 3 occupying its full width which has been produced by removing layer 20 completely in a pattern of lines, and is covered by a further transparent layer 2 consisting of $MgF_2$ which is 342 nm thick and has a refractive index of 1.38. The grating depth thus corresponds to the thickness of layer 20, and is 285 nm. The grating period $\Lambda(x)$ varies linearly in a direction normal to the grating lines, increasing from $\Lambda_1$=970 nm to $\Lambda_2$=977 nm.

When producing the coupler, layers 20 and 2 can be applied as described in connection with the first example of an evanescent field sensor plate. Production of the coupling grating 3 after application of the layer 20 also occurs as described there. In this operation, a phase mask is used whose grating varies appropriately, hence linearly in the present case. Such phase masks can be produced by appropriately bending a flexible master copy and applying a grating structure using the two-beam interference method. The phase mask is derived by replication, that is, by making an impression of the reflattened master copy.

The coupler can advantageously be used in a device for monitoring and stabilising the wavelength of a laser 28 (FIG. 14) the light of which is fed into a light-conducting fibre 29, for instance a glass fibre, of a fibre network. The device comprises a semi-transmissive mirror 30 arranged in the path of the light beam coming from the laser 28, followed by a first optical system 31 to expand, and a second optical system 32 to collimate the part of the light beam deflected by the mirror 30. Following after the optical systems, the coupler 23 described above is arranged in the light beam normal to the beam direction, in such a way that the beam strikes the coupling grating 3. Mounted directly beneath the coupler 23 is a detector system with two photo-detectors 33a and b which are arranged so as to be immediately adjacent one behind the other and normal to the lines in such a way that the part of the light beam transmitted by a first portion of the coupling grating 3 where the grating period is between $\Lambda_1$ and an intermediate value $\Lambda_i$ strikes the first photodetector 33a while the part transmitted by the remaining portion of the coupling grating 3 where the grating period is between $\Lambda_i$ and $\Lambda_2$ strikes the second photodetector 33b. The photodetectors 33a and b can be displaced so that $\Lambda_i$ is adjustable.

Figure 15:
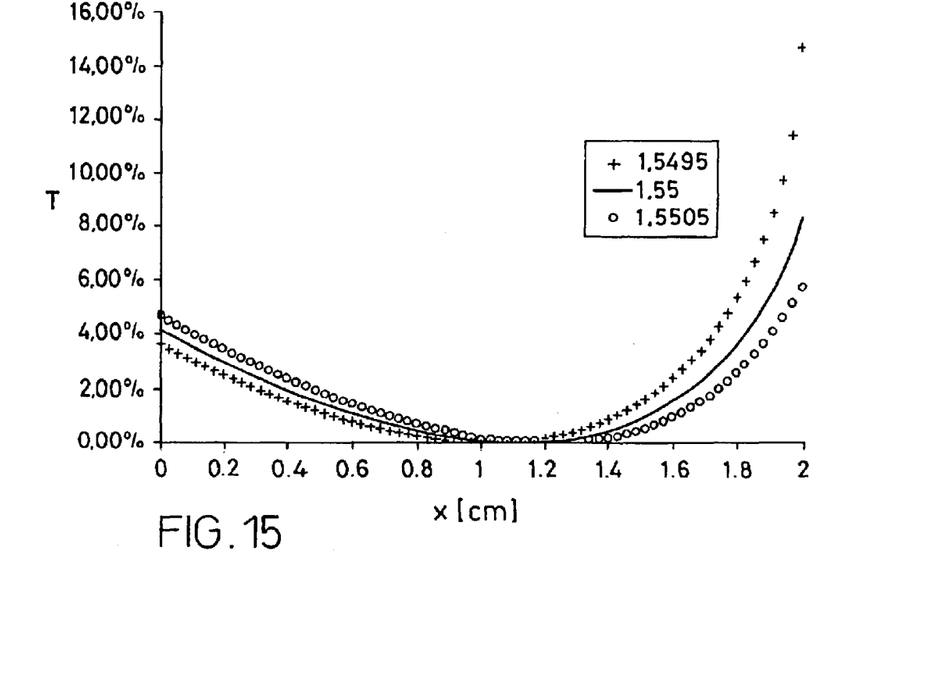
FIG. 15 shows the transmissivity of the coupler according to the third embodiment as a function of its position on the coupling grating at different wavelengths.

The transmissivity of the coupler 23 is a sensitive function of wavelength and of the grating period $\Lambda$. Because of the position-dependent variation of the grating period $\Lambda(x)$, therefore, it exhibits a specific wavelength dependence for the incident light which depends on its position. This is shown in FIG. 15, where the transmissivity T can be gathered as a function of position on the coupling grating 3 for three very close wavelengths (1549.5 nm, 1550 nm, 1550.5 nm). The minimum of the transmissivity curve shifts to larger or smaller grating periods as the wavelengths increase or decrease, and hence to a different position on the grating. This in turn gives rise to changes in the relative intensities of the light captured by the photo-detectors 33a and 33b, which has a direct effect on the size of their output signals $I_a$, $I_b$.

Figure 14:
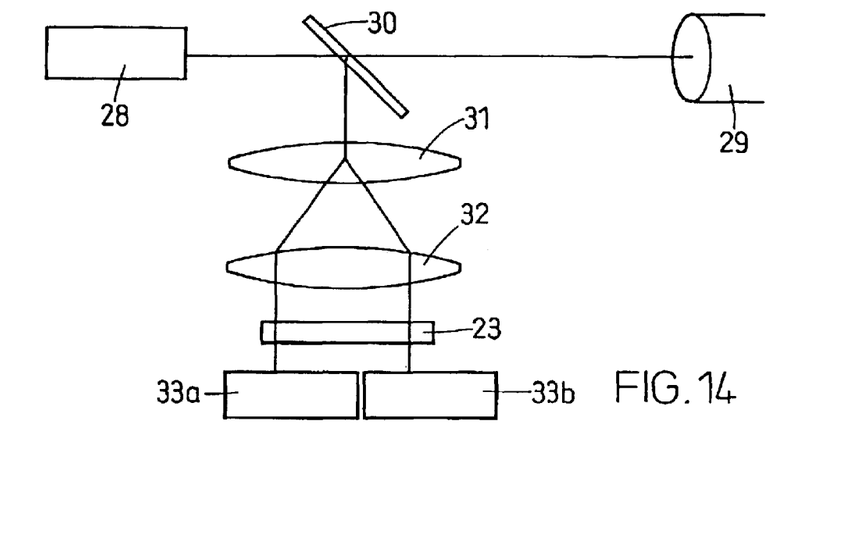

For the purposes of stabilising a particular wavelength, one can then roughly adjust the position of the detector arrangement in accordance with the wavelength of interest, and then calculate a value $$Q=(I_a-I_b)/(I_a+I_b)$$

and reduce it to zero by shifting the detector arrangement. Any change in wavelength of the light beam coming from the laser 28 will give rise to a positive or negative deviation of the value of Q from zero, depending on the direction of the wavelength change, and can be compensated by corresponding control of the laser 28. The intensity of the light beam is unimportant here. Only the intensity distribution of the expanded light beam which may not be homogeneous but follow a gaussian distribution, for instance, might eventually cause perturbations, but this can then be compensated by appropriate arrangement or extension of the optical systems or by calculation.

The optical elements according to the invention can be modified in many respects without departing from the basic concept of the invention. Thus, in many cases deviations from the mean value of up to 0.3° or even up to 0.5° over the entire element or even over a coupling grating can be admitted. For the evanescent field sensor plates, too, it will often be sufficient when the changes in coupling angle $\Theta$ along the grating lines are not larger than 0.1°/cm.

Many deviations or special adaptations to particular requirements are possible as well in the production process. Thus, even in the exposure step which is decisive for the process, the photoresist layer may by spaced apart from the phase mask, which facilitates the process. However, it must be arranged in the near field, that is, at a distance which as a rule is smaller than 100 μm, for the diffraction pattern to be sufficiently pronounced. This distance may perhaps be between 2 μm and 100 μm. Instead of a mercury-vapour lamp, a laser can also be used as the light source, particularly an excimer laser or an argon laser. Apart from $Ta_2O_5$, other substances can be used as materials for the layer, particularly $Nb_2O_5$, $TiO_2$, $ZrO_2$, $Al_2O_3$, $SiO_2$—$TiO_2$, $HfO_2$, $Y_2O_3$, $SiO_xN_y$, $Si_3N_4$, $HfO_xN_y$, $AlO_xN_y$, $TiO_xN_y$, $MgF_2$ oder $CaF_2$. Ion-enhanced evaporation or plasma-enhanced gas phase deposition can be used as coating methods. Finally, several layers differing in their composition and thickness can be applied consecutively, as described in one of the embodiments portrayed.

Phase masks need not be produced directly by the two-beam interference method but can be copied directly or indirectly from a master copy thus produced. They can be used several times with layers interrupted in diverse manner when diverse arrangements of coupling gratings and the like are to be generated while maintaining a constant grating period. Instead of a nontransparent layer, a suitable layer of transparent material can also be used. Thus, the grooves of the grating can be filled by a material having the refractive index of the phase mask substrate.

The phase mask can be antireflection-coated. In this case it may not be necessary to apply a reflection-reducing layer to the photoresist layer, which facilitates the production of series of grating structures on the substrates. For antireflection, a layer having a refractive index between that of the phase mask substrate and that of air, and for instance consisting of $MgF_2$, is applied to the side of the phase mask facing the photoresist layer. At the same time the grating must be adjusted in such a way that the interfering diffraction orders of the transmitted light will again have the same intensity. This adjustment can occur by changing the groove-to-land ratio and the grating depth, which are readily calculated with the aid of programmes known among experts.

List of Reference Symbols

1 Substrate
2 Transparent layer
3 Coupling grating
4 Added top part
5 Cover plate
6 Opening
7 Tube section
8 Cavity
9 Optical system
10 Photoresist layer
11 Mercury-vapour lamp
12 Optical system
13, 13' Folding mirror
14 Phase mask
15 Quartz substrate
16 Photoresist layer
17 Chromium layer
18 Photoresist layer
19 Glass plate
20 Layer
21a,b Stripe waveguides
22 Coupling region
23 Coupler
24 Input
25a,b,c Outputs
26a,b Optical fibres
27 Photodetector
28 Laser
29 Optical fibre
30 Semi-transmissive mirror
31 First optical system
32 Second optical system
33a,b Photodetectors

What is claimed is:

1. Evanescent field sensor plate with a platelike substrate with, on a surface portion, a plurality of continuous coupling gratings each formed as a line grating with a grating period between 150 nm and 2000 nm, the coupling gratings being parallel to each other and extending over at least 0.5 cm, and the platelike substrate bears a transparent layer with a refractive index different from that of the substrate, wherein a coupling angle ($\theta$) at which a light beam directed through the substrate to the coupling grating is coupled with the transparent layer with maximum coupling efficiency changes by at most 0.05°/cm along the line grating and the absolute value of deviation of the coupling angle ($\theta$) from a required value on the evanescent field sensor plate does not exceed 0.5°.

2. Evanescent field sensor plate according to claim 1, wherein an extension of the coupling grating along the line grating is at least 1 cm.

3. Evanescent field sensor plate according to claim 1, wherein the surface area of the coupling grating is at least 10 $cm^2$.

4. Evanescent field sensor plate according to claim 1, wherein the coupling angle ($\theta$) changes by at most 0.05°/cm along the line.

5. Evanescent field sensor plate according to claim 1, wherein the absolute value of deviation of the coupling angle ($\theta$) from its mean value on the evanescent field sensor plate does not exceed 0.3°, and preferably does not exceed 0.15°.

6. Evanescent field sensor plate according to claim 1, wherein the refractive index of the transparent layer is between 1.65 and 2.80.

7. Evanescent field sensor plate according to claim 1, wherein the transparent layer consists of $Ta_2O_5$, $Nb_2O_5$, $TiO_2$, $ZrO_2$, $Al_2O_3$, $SiO_2$—$TiO_2$, $HfO_2$, $Y_2O_3$, $SiO_xN_y$, $Si_3N_4$, $HfO_xN_y$, $TiO_xN_y$, $MgF_2$ or $CaF_2$.

8. Evanescent field sensor plate according to claim 1, wherein the thickness of the transparent layer is between 50 nm and 200 nm.

9. Evanescent field sensor plate according to claim 1, wherein a groove-to-land ratio of the at least one coupling grating is between 0.3:1 and 3:1, preferably between 1.7:1 and 1.5:1.

10. Evanescent field sensor plate according to claim 1, wherein a grating depth of at least one coupling grating is between 5 nm and 75 nm.

11. Evanescent field sensor plate according claim 1, wherein an at least one coupling grating covers only part of the surface of the evanescent field sensor plate while the remaining part remains free.

12. Evanescent field sensor plate according to claim 1, further comprising; at least one coupling grating formed as a strip extending in parallel to the lines, essentially over the entire width or length of the evanescent field sensor plate.

13. Evanescent field sensor plate according to claim 1, wherein several coupling gratings in the form of strips are arranged at a distance parallel to each other.

14. Microtitre plate with an evanescent field sensor plate according to claim 1 as well as with an added honeycomb-shaped top part which laterally defines each of a plurality of cavities arranged in a regular array, the bottom of each of the cavities formed by the evanescent field sensor plate.

15. Optical coupler for communications technology with a platelike substrate with, on a surface portion, a plurality of continuous coupling gratings each formed as a line grating with a grating period between 150 nm and 2000 nm, the coupling gratings being parallel to each other and extending over at least 0.5 cm and the platelike substrate bears a transparent layer with a refractive index different from that of the substrate, wherein a coupling angle ($\theta$), at which a light beam directed through the substrate to the coupling grating is coupled to the transparent layer with maximum efficiency, has an absolute value of deviation from a required value on the coupling grating, the deviation does not exceed 0.5°.

16. Coupler according to claim 15, wherein an extension of the coupling grating along the line grating is at least 1 cm.

17. Coupler according to claim 15, wherein a surface area of the coupling grating is at least 10 cm$^2$.

18. Coupler according to claim 15, wherein the coupling angle (θ) changes by at most 0.1°/cm along the line of the coupling grating.

19. Coupler according to claim 18, wherein the coupling angle (θ) changes by at most 0.05°/cm along the line.

20. Coupler according to claim 15, wherein the absolute value of deviation of the coupling angle (θ) from its mean value on the surface portion does not exceed 0.3°, and preferably does not exceed 0.15°.

21. Coupler according to claim to claim 15, wherein the refractive index of the transparent layer is between 1.65 and 2.80.

22. Coupler according to claim 15, wherein the transparent layer consists of $Ta_2O_5$, $Nb_2O_5$, $TiO_2$, $ZrO_2$, $Al_2O_3$, $SiO_2$—$TiO_2$, $HfO_2$, $Y_2O_3$, $SiO_xN_y$, $Si_3N_4$, $HfO_xN_y$, $AlO_xN_y$, $MgF_2$ or $CaF_2$.

23. Coupler according to claim 15, wherein a thickness of the transparent layer is between 50 nm and 200 nm.

24. Coupler according to claim 15, wherein a groove-to-land ratio of the at least one coupling grating is between 0.3:1 and 3:1, preferably between 1.7:1 and 1.5:1.

25. Coupler according to claim 15, wherein a grating depth of the at least one coupling grating is between 5 nm and 75 nm.

26. Coupler according to claim 15, wherein a surface portion bears at least two regular coupling gratings with different grating periods.

27. Coupler according to claim 15, wherein a surface portion bears at least one irregular coupling grating in which the distance between neighboring grating lines is not constant.

28. Coupler according to claim 27, wherein in the irregular coupling grating the grating period changes linearly in a direction normal to the lines only.

29. Device for monitoring a wavelength with a coupler according to claim 27 as well as with a detector assembly arranged directly beneath the coupler, the device having at least two photodetectors arranged consecutively normal to the lines.

30. Device according to claim 29, wherein the detector arrangement is displaceable in a direction normal to the lines relative to the coupler.

* * * * *